United States Patent [19]

Bauer et al.

[11] Patent Number: 5,691,388

[45] Date of Patent: Nov. 25, 1997

[54] METHOD OF DECOMPOSING POLYCYANURATE-CONTAINING MATERIALS

[75] Inventors: Monika Bauer; Jörg Bauer, both of Berlin; Karin Göcks, Zeuthen, all of Germany

[73] Assignee: Fraunhofer-Gesellschaft Zur Forderung der Angewandten Forschung e.v., Munich, Germany

[21] Appl. No.: 646,290

[22] PCT Filed: Sep. 7, 1995

[86] PCT No.: PCT/DE95/01236

§ 371 Date: Jun. 21, 1996

§ 102(e) Date: Jun. 21, 1996

[87] PCT Pub. No.: WO96/08530

PCT Pub. Date: Mar. 21, 1996

[30] Foreign Application Priority Data

Sep. 16, 1994 [DE] Germany ............... 44 32 965.2

[51] Int. Cl.$^6$ ............................... C08J 11/14
[52] U.S. Cl. ............................. 521/49.5; 521/49
[58] Field of Search ........................ 521/49.5, 49

[56] References Cited

U.S. PATENT DOCUMENTS

| | | | |
|---|---|---|---|
| 2,545,049 | 3/1951 | Schaefer et al. | 260/249.6 |
| 3,404,103 | 10/1968 | Matsudaira et al. | 521/49.5 |
| 3,983,087 | 9/1976 | Tucker et al. | 521/49.5 |
| 4,039,568 | 8/1977 | Sakai et al. | 521/49.5 |
| 4,110,266 | 8/1978 | Sheratte | 521/49.5 |
| 4,162,995 | 7/1979 | Sheratte | 521/49.5 |

FOREIGN PATENT DOCUMENTS 3820597  12/1989  Germany .

OTHER PUBLICATIONS

*Synthesis*, 1975, Stuttgart, DE, "Partielle Aminolyse von 2,4,6–triazin. Teil 1: Herstellung von 2–Alkyl(–en)amino–4, 6–diallyl–oxy–s–triazinen", H. Anhe et al., pp. 182–186.

*Journal f. prakt. Chemie*, 1981, Band 323, Heft 4, "Einfache Synthesen fur Amino–aroxy–1,2,5–tiazine", D. Martin et al., pp. 694–699.

*Primary Examiner*—Ralph H. Dean
*Attorney, Agent, or Firm*—Weingarten, Schurgin, Gagnebin & Hayes LLP

[57] ABSTRACT

The invention concerns a method of decomposing materials containing polycyanurates, the method calling for the polycyanurate-containing materials to be converted, in a first operation, into a finely divided form and then, in a second operation, aminolysed with an agent containing at least one reactive $NH_2$ group.

12 Claims, No Drawings

METHOD OF DECOMPOSING POLYCYANURATE-CONTAINING MATERIALS

FIELD OF THE INVENTION

The invention concerns a process for decomposing materials containing polycyanurate, especially polycyanurates, polycyanurate prepolymers and plastics containing polycyanurate.

BACKGROUND OF THE INVENTION

Polycyanurates can be produced by polycyclotrimerization of di- or polyfunctional cyanates. Because of their good electrical properties, especially insulating properties, their resistance to chemicals and moisture and their heat stability, they are used, inter alia, as inclusion products for electronic components and in adhesive, casting and laminating technology. To modify their properties, the polycyanurates are mixed with various additives, for example, soot, silicates or aluminum oxide and/or combined with other polymer compounds.

Direct recycling of materials containing polycyanurates, from plastic waste or production residues, is not possible due to the duroplastic properties of the polycyanurates. It is possible to mix finely ground production wastes in quantities of 15% to 30% with new products as fill. The usual method of disposal therefore consists of dumping or burning materials containing polycyanurate.

Methods of purposeful recycling of plastic materials have not been researched very much to date. Thermolysis, pyrolysis and hydrating methods are known, in which, depending on the reaction conditions (and catalysts added), synthesis gases and petroleum-like products are obtained, but, for the most part, they have lost the chemical structure present in the primary material. These products can be reused as primary materials in the chemical industry, but only by losing a high proportion of energy and chemical specificity compared to the original monomer primary materials.

For polyesters and polyamides, alcoholysis methods have become known, in which they are decomposed into monomers or oligomers. This method cannot be used on materials containing polycyanurates. A similar process for polycyanurate has not been known.

U.S. Pat. No. 2,545,049 describes a method of aminolysis of dissolved or suspended cyanuric acid triaryl esters, in which, depending on the reaction conditions, one to all aryl oxy groups can be exchanged for amino groups; see also D. Martin et al., Journal für praktische Chemie 723:694 (1981). Moreover, partial aminolysis of melted cyanuric acid triaryl esters is known from H. Ahne et al., Synthesis 182:184 (1975). But the primary products and reaction conditions of these known reactions are extremely special, so that these methods do not appear to be usable in general on plastics containing groups of polycyanurates with complete aminolysis of all units.

In general, it would be desirable to find a method with which materials containing polycyanurate, i.e., polycyanurates, polycyanurate prepolymers and plastics containing polycyanurates, could be decomposed so that mainly monomer products with a definite chemical composition are obtained. It would also be desirable if the products occurring in this decomposition could be used, at least partially, as primary products for new polycyanurates or other polymers, especially those with related structures.

The invention is therefore based on the task of providing a method with which materials containing polycyanurate can be decomposed so that definite recyclable products can be obtained while largely maintaining the structure of the components present in the material containing polycyanurates.

SUMMARY OF THE INVENTION

This task is solved with a method in which the material containing polycyanurate is dissolved in a solvent or finely ground in a first step and thereby put into a finely distributed form and, in the second step, is subjected to aminolysis with an agent containing at least one reactive $NH_2$ group.

The reactive $NH_2$ or amino group in the sense of the invention is understood to be any amino group that is capable of inducing an aminolysis reaction on polycyanurate. These are, specifically, ammonia, hydrazine, primary amines and primary hydrazines with aliphatic or aromatic radicals, which can in turn be substituted. The reaction therefore involves any primary amines of saturated or unsaturated, straight, branched or cyclic aliphatic or aromatic hydrocarbons, the corresponding hydrazines, and naturally ammonia and hydrazine themselves. The branching or chain length of the hydrocarbon radicals has no role in the reaction, so long as the amino function has sufficient reactivity to the cyanurate groups.

The primary amines used can have other substituents, depending on the desired substitution pattern of the reaction product. Another amino function is especially advantageous. Moreover, there can be one or more hydroxy functions, and any other substituents desired, so long as they do not have a negative effect on the reaction. Accordingly, the compound used with a reactive $NH_2$ group has the general formula $NH_2$—X, wherein X stands for hydrogen, OH, $NH_2$, $R^1$ or $NHR^1$ and $R^2$ is an aliphatic or aromatic hydrocarbon radical with especially 1 to 20 carbon atoms, which can be substituted. X can also be especially an $R^2$-Y group, wherein $R^2$ is a bivalent aliphatic or aromatic hydrocarbon radical with especially 2 to 20 carbon atoms and Y stands for any bivalent radical, but especially for $NH_2$, $NHR^1$ or OH.

In the method in the invention, the primary materials containing polycyanurate are decomposed by an agent containing at least one reactive $NH_2$ group into low-molecular components containing triazine and di- or polyfunctional alcohols, which can be recycled after corresponding conversion.

The materials containing polycyanurates used in the invention basically have the following structural element shown in formula I.

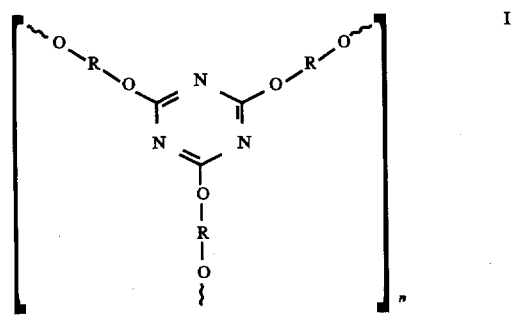

Prepolymers containing polycyanurate, as are frequently used in plastics technology, have, for example, the structural element in formula II.

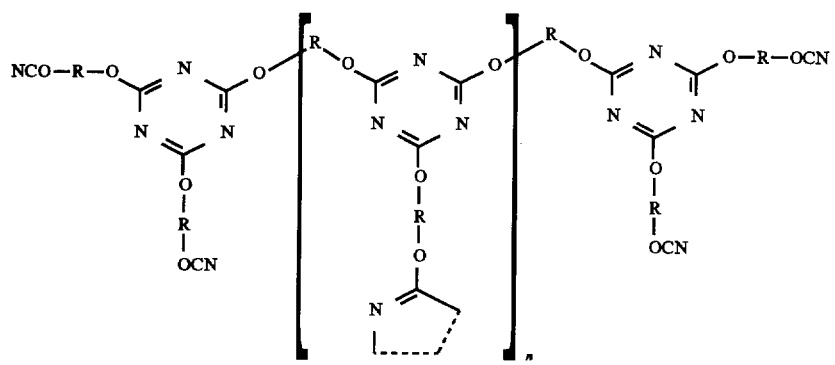

Such materials containing polycyanurate, i.e., the finished plastics and also the prepolymers, can, for example, be obtained from compounds with formulas III to V, in which the cyanate groups of a compound bivalent radical correspond to the radical R in formulas I and II.

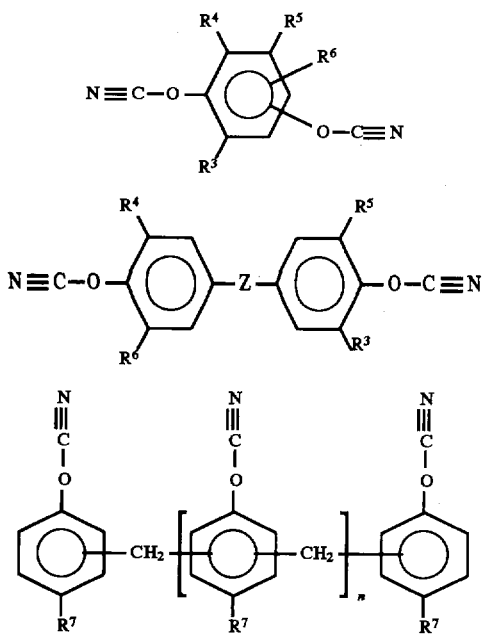

wherein $R^3$ to $R^6$ are, independently from one another, H, $C_1$–$C_{10}$-alkyl, $C_3$–$C_8$-cycloalkyl, $C_1$–$C_{10}$-alkoxy, halogen or phenyl, wherein alkyl or aryl groups can be fluorinated or partially fluorinated; Z is a chemical bond, $SO_2$, $CF_2$, $CH_2$, $CH(CH_3)$, isopropyl, hexafluoroisopropyl, alkyl, O, $NR_1$, N=32 N, CH=CH, CO—O, CH=N, CH=N—N=CH, alkyl-O-alkyl with $C_1$–$C_8$-alkyl, dicyclopentadienyl, S, $C(CH_3)_2$ or $C(CH_3)_2$-phenyl-$C(CH_3)_2$; and $R^7$ is H, $C_1$–$C_{10}$-alkyl and n is 0 to 20.

Other di- and polycyanates for producing plastic materials containing polycyanurate are known; materials containing polycyanurate derived from them can also be decomposed according to the invention.

The method in the invention basically produces products with structural formulas VI A and VI B

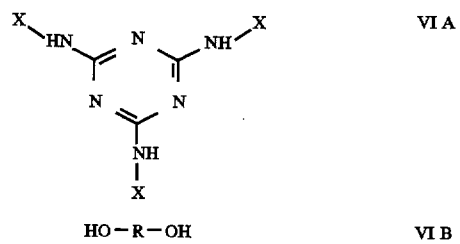

where X is defined as above and R is a connecting group, which comes from the monomers used for production.

DETAILED DESCRIPTION OF THE INVENTION

For the method in the invention, it is essential that the material containing polycyanurate be in finely distributed form. This can be done by dissolving the material in an appropriate solvent, for example, in a cyclic ether like THF, a chlorinated hydrocarbon like methylene chloride, or a solvent containing nitrogen, for example pyrrolidone or NMP. For the solvent, the compound containing $NH_2$ used for aminolysis can also be used, for example, ammonia or primaryamine, if necessary in condensed form under pressure or melted.

If the plastic materials are not soluble, fine grinding and suspension in a solvent or reactive agent is helpful. Average particle sizes of <500 μm and especially <100 μm have proven useful. Grinding can also be useful for soluble materials that contain non-soluble additives.

The method in the invention can be used at temperatures from −20° C. to +200° C., but especially up to the boiling point of the solvent or agent used. If the reaction is carried out under pressure with gaseous agents like $NH_3$ or lower amines, the temperature can also be raised over the boiling point of the amine used. The reaction speed depends on the temperature, the state of distribution of the material containing polycyanurate and the solvent used, wherein with finely distributed materials (solution) at high temperatures directly in the reactive agent an extremely fast reaction can be achieved within a few hours or less than 1 hour. By using appropriate diamines or amino alcohols, the method in the invention can be used to obtain di- and/or polyfunctional amines and/or alcohols, which can be used as primary materials for the production of polyurethanes, melamine resins, epoxy resins, polyesters, polycarbonates, etc. Di- and polyfunctional phenols produced can be reconverted into corresponding di- and polyfunctional cyanates, which can be used as primary materials for new materials containing polycyanurate, so that one can speak of real recycling.

The invention will be described in greater detail using the following examples of embodiment.

EXAMPLE 1

Equimolar quantities of a DCBA-based prepolymer with 50% conversion of cyanate groups and ethyl amine were dissolved in tetrahydrofurane (THF) into 10%/wt. solutions. The solutions were purified and stored at 253° K. for 5 days.

The prepolymer was proven to be completely decomposed by means of gel permeation chromatography (GPC), and all products of decomposition had a mol mass of less than 1000.

EXAMPLE 2

Equimolar quantities of a DCBA-based prepolymer with 50% conversion of cyanate groups and dodecylamine were dissolved in THF, and 15%/wt. solutions were obtained. The solutions were purified and stored for one day at room temperature.

Complete decomposition of the prepolymer was shown by means of GPC, wherein all products of decomposition had a mol mass of less than 1000. The same result was able to be obtained under otherwise equal conditions with dichloromethane as the solvent.

EXAMPLE 3

Hardened polycyanurate on a dicyanatobisphenol-A (DCBA) base and aminohexanol were suspended or dissolved in THF, and a 50% additive of aminohexanol was used. The treated material was boiled 66 hours at 339° K. with reflux.

Complete decomposition of the polycyanurate was able to be shown by means of GPC, and all products of decomposition had a mol mass of less than 1000.

EXAMPLE 4

To 10.8 mg of pulverized, hardened DCBA-based polycyanurate with a particle size of <100 μm was added 53.4 mg of aminohexanol, and the treated material was heated to 50° C. in a water bath for 30 minutes.

Under the conditions specified, complete aminolysis of the polycyanurate occurred. All products of decomposition had a mol mass of less than 1000 (GPC).

EXAMPLE 5

To 10.8 mg of granulate with a particle size <500 μm of hardened DCBA-based polycyanurate was added 53.4 mg of aminohexanol, and the treated material was heated for 20 hours to 65° C. in a water bath. Complete decomposition of the polycyanurate was able to be shown by means of GPC, and all products of decomposition had a mol mass less than 1000.

We claim:

1. A method of decomposing polycyanurate-containing materials, comprising the steps of:
   dissolving or finely grinding a material containing polycyanurate; and
   subjecting said dissolved or finely ground polycyanurate-containing material to aminolysis with an agent consisting essentially of a compound containing at least one reactive $NH_2$ group.

2. A method of decomposing polycyanurate-containing materials, comprising the steps of:
   dissolving or finely grinding a material containing polycyanurate; and
   subjecting said dissolved or finely ground polycyanurate-containing material to aminolysis with an agent comprising a hydrazine compound.

3. The method of claim 1, wherein said agent containing at least one reactive $NH_2$ group is a primary aliphatic or aromatic amine or hydrazine, and wherein further said primary aliphatic or aromatic amine or hydrazine can have other functional groups.

4. The method of claim 1, wherein said agent containing at least one reactive $NH_2$ group is an amino alcohol with the formula $NH_2$—Y—OH, wherein Y is a bivalent aliphatic or aromatic radical.

5. The method of claim 1, wherein said agent containing at least one reactive $NH_2$ group is a diamine with the formula $NH_2$—Y—$NH_2$, wherein Y is a bivalent aliphatic or aromatic radical.

6. The method of claim 1, wherein said aminolysis step is carried out in a solvent.

7. The method of claim 6, wherein said solvent is a cyclic ether, chlorohydrocarbon or solvent containing N.

8. The method of claim 7, wherein said solvent is THF, $CH_2Cl_2$ or NMP.

9. The method of claim 1, wherein said agent containing at least on reactive $NH_2$ group is used as a solvent, if necessary under pressure in the condensed state or after melting.

10. The method of claim 1, wherein said material containing polycyanurate is ground to a grain size less than 500 μm.

11. The method of claim 1, wherein said material containing polycyanurate is ground to a grain size less than 100 μm.

12. The method of claim 1, wherein said aminolysis step is carried out at high temperature.

* * * * *

UNITED STATES PATENT AND TRADEMARK OFFICE
CERTIFICATE OF CORRECTION

PATENT NO. : 5,691,388
DATED : November 25, 1997
INVENTOR(S) : Monika Bauer, et al.

It is certified that error appears in the above-identified patent and that said Letters Patent is hereby corrected as shown below:

Column 1, line 50, "723:694" should read --323:694--.

Column 3, line 54, "N=32N," should read --N=N,--.

Column 4, line 41, "primaryamine" should read --primary amine--.

Signed and Sealed this

Fifteenth Day of May, 2001

Attest:

NICHOLAS P. GODICI

Attesting Officer          Acting Director of the United States Patent and Trademark Office